US005738824A

United States Patent [19]
Pfeifer

[11] Patent Number: 5,738,824
[45] Date of Patent: Apr. 14, 1998

[54] METHOD FOR THE TESTING AND CLEANING OF INSTRUMENTS FOR MINIMAL INVASIVE SURGERY OR MINIMAL INVASIVE EXAMINATION OF BODY CAVITIES

[75] Inventor: Egbert Pfeifer, Waldkraiburg, Germany

[73] Assignee: Netzsch Newamatic GmbH, Waldkraiburg, Germany

[21] Appl. No.: 554,510

[22] Filed: Nov. 7, 1995

[30] Foreign Application Priority Data

Nov. 11, 1994 [DE] Germany ............... 44 40 363.1

[51] Int. Cl.⁶ ................................................ G05D 7/00
[52] U.S. Cl. ..................... 422/3; 73/37.5; 134/18; 134/22.12; 134/22.18; 422/20; 422/28; 422/33; 422/105; 422/108; 422/110
[58] Field of Search ................ 422/1, 3, 20, 33, 422/28, 105, 119, 108, 110, 111; 134/8, 22.1, 22.11, 22.12, 22.13, 22.14, 22.18, 18; 73/37.5, 37.9, 49.5

[56] References Cited

U.S. PATENT DOCUMENTS

| | | | |
|---|---|---|---|
| 4,064,886 | 12/1977 | Heckele | 422/1 X |
| 4,763,678 | 8/1988 | Ott | 422/300 X |
| 5,225,160 | 7/1993 | Sanford et al. | 422/1 X |
| 5,558,841 | 9/1996 | Nakagawa et al. | 422/105 |

FOREIGN PATENT DOCUMENTS 3918432  3/1992  Germany.
2275341  8/1994  United Kingdom.

OTHER PUBLICATIONS

"Endoskop–Aufbereitung Problematik und Stand der Technik", Krankenhaus Technik Journal, May 1991, pp. 32–34, 39.

*Primary Examiner*—Krisanne Thornton
*Attorney, Agent, or Firm*—Baker & Botts

[57] ABSTRACT

For the testing and cleaning of instruments (20) with continuous channels (25) for minimal invasive surgery or minimal invasive examination of body cavities, use is made of a testing and cleaning tray (10) for the instruments (20), which testing and cleaning tray (10) has flushing channels (30; 31), and of a holder arrangement (41) which receives this tray (10) and has attachments for each flushing channel (30). A fluid source (47) is connected via a distributor (56) to valves (57) and to the attachments of the holder arrangement (41). Using a throughput testing device (46; 55), the channels (25) of the instruments (20) are tested for penetrability individually or in groups one after another by means of fluid from the fluid source (47) being conveyed to the channels (25). In the event of the throughflow of a channel (25) being insufficient, the instrument (20) in question is registered for rejection, and in the event of the throughflow being sufficient, the instruments (20) are re-flushed with disinfecting and/or cleaning agents.

11 Claims, 3 Drawing Sheets

METHOD FOR THE TESTING AND CLEANING OF INSTRUMENTS FOR MINIMAL INVASIVE SURGERY OR MINIMAL INVASIVE EXAMINATION OF BODY CAVITIES

BACKGROUND OF THE INVENTION

The invention relates to a method for the testing and cleaning of instruments for minimal invasive surgery or minimal invasive examination of body cavities.

The introduction of minimal invasive surgery (MIS) and of minimal invasive procedures for the examination of body cavities, using surgical and diagnostic instruments specially developed for these areas of application, has revolutionized examining and operating practice in important areas. These instruments are passed through natural or surgically created openings of small diameter into body cavities, such as the intestines or abdominal cavity, to their location of use, so that examinations and minor surgical interventions are possible with substantially less stress being imposed on the patient, for example without general anesthesia.

The class of instruments for minimal invasive surgery (MIS) and minimal invasive examination of body cavities includes non-flexible shaft instruments made of stainless steel as well as flexible instruments which are usually made of aluminum and high-flexibility plastics.

Non-flexible instruments are used for minimal invasive surgery and are accordingly referred to as MIS instruments. They have a single channel of small diameter inside an elongate shaft and, together with devices which are provided on the instruments and which can be manipulated by means of a plunger running inside the channel, they allow surgical interventions, such as, for example, removal of the gallbladder.

Flexible instruments, so-called endoscopes, are used in particular for diagnostic purposes, and they have a multiplicity of channels and capillary tubes in their interior.

The use of surgical and diagnostic single-use instruments should be avoided as far as possible on economic and environmental grounds. It is therefore necessary to develop methods for treating such instruments, which methods guarantee efficient cleaning, disinfection and sterilization satisfying the strict clinical requirements. While the external surfaces and joints of such instruments can be cleared of trapped contaminating material in a simple and effective manner by ultrasound treatment, the flushing-through and subsequent cleaning and sterilization of one or more channels in tubular components represents a critical treatment step in terms of observing the stringent hygiene regulations.

For flexible endoscopes which have a plurality of channels, particularly in the interior of the flexible areas, and which for this reason present corresponding problems during cleaning and sterilization, methods and devices have been developed which are intended to permit cleaning, disinfection and sterilization corresponding to the strict hygiene requirements. In the journal called "Krankenhaus Technik" [Hospital procedures], May 1991 issue, p. 32 to 39, a method for the testing, cleaning and disinfection of endoscopes is described in which the channels of the instruments are connected to a fluid source for chemical and heat treatment, cleaning with concentrated washing and disinfecting solutions at high temperature, and with subsequent sterile re-flushing. Since the endoscope channels are flushed through within a closed system which also includes the fluid source, the channels can also be tested for leakproofness, during the procedure, without any great outlay.

However, testing the penetrability of all the channels within an endoscope is not possible within the scope of this method. For this reason, it is not possible, upon completion of such a procedure, to rule out with certainty the possibility that some of the channels were obstructed throughout the entire procedure and as a consequence were not accessible for cleaning and sterilization.

A method for disinfection of endoscopes is disclosed in DE 3 918 432 C2, in which method a channel of such an instrument is connected to a fluid source, the channel is tested for penetrability by means of fluid being delivered to it from the fluid source, and if there is too little or no throughflow, the instrument in question is recognized as being one that cannot be adequately flushed and is registered for rejection, and if the throughflow is sufficient, the instrument in question is recognized as being one that can be flushed and it is re-flushed with disinfecting and/or cleaning agents. In the event of the flushability being insufficient, the penetrability of the channel is restored manually.

A method for checking cavities or channels in turbine blades is known from GB 2 275 341 A, in which method the flow rate of a fluid through these cavities or channels is determined, and the data obtained are compared with known values. The result of this comparison is used for establishing whether solid material from the manufacturing method is located in the cavities or channels and, if appropriate, to what extent there is a blockage.

Instruments of varying dimensions for minimal invasive surgery and for minimal invasive procedures for examination of body cavities are currently used in hospitals in various areas of application. These instruments differ from each other particularly in terms of the number and the diameters of the channels which are provided in them. In order to observe the stringent hygiene requirements when cleaning the instruments, and in particular to guarantee complete penetrability of all the channels and capillary tubes as a precondition for complete cleaning, it would be desirable to adapt the test parameters and if appropriate also the cleaning conditions to the individual device type.

There is therefore a need for a testing, cleaning and disinfecting method for instruments for minimal invasive surgery and minimal invasive examination of body cavities belonging to different device types, which method makes it possible to guarantee the penetrability of all the channels and capillary tubes in the interior of each individual instrument and, as a consequence, to guarantee a complete cleaning and disinfection in compliance with stringent hygiene regulations.

In addition to this, it is desirable to carry out a method of this kind in such a way that the testing and cleaning conditions can be adapted individually to each instrument type, and such that this can be done fully automatically, i.e. without intervention of personnel.

SUMMARY OF THE INVENTION

The object of the invention is to provide a method and an arrangement for the testing, cleaning and disinfecting of instruments for minimal invasive surgery and minimal invasive examination of body cavities, by means of which method and arrangement contaminated instruments of various designs can be tested for complete penetrability of all their channels and capillary tubes extending in them, and can be cleaned and disinfected in compliance with stringent hygiene regulations.

A further object of the invention is to provide such a method and such an arrangement in such a way that the testing and cleaning conditions can be adapted for each instrument type individually and fully automatically, i.e. without intervention of personnel.

The invention relates to a method for the testing and cleaning of one or more instrument(s) for minimal invasive surgery or minimal invasive examination of body cavities, with in each case at least one continuous channel, in which method (a) the channel of the or each instrument is connected to a fluid source;

(b) the channel is tested for penetrability;

(c) if there is too little or no throughflow, the instrument in question is recognized as being one that cannot be adequately flushed and is registered for rejection, and (d) if the throughflow is sufficient, the instrument in question is recognized as being one that can be flushed and it is re-flushed with disinfecting and/or cleaning agents, wherein the channel is tested for penetrability by means of fluid being delivered to it from the fluid source, a quantity of the fluid flowing through the channel in one unit of time being determined, and the fluid volume determined being compared with preset data specific to the device, and wherein, on the basis of the result of the penetrability test, the instrument or instruments in question is/are identified in terms of its/their device type, and, as a function of this, conditions are established for the re-flushing with disinfecting and/or cleaning agents.

The invention is based on the knowledge that instruments for minimal invasive surgery and minimal invasive examination of body cavities can be identified on the basis of a fluid volume flowing through all the channels and capillary tubes of an instrument in a unit of time. The fluid volume flowing through the channel and capillary tube system of such an instrument in a unit of time is determined directly by the number and the internal diameter of these channels and capillary tubes and is thus characteristic for the instrument type, so that if this characteristic is known, the device type can be ascertained without difficulty by comparison with a standard value defined beforehand for the device type.

In a preferred embodiment of the method according to the invention, the instruments which are to be cleaned are checked individually for penetrability. This is particularly suitable if instruments of different instrument types are to be cleaned in a joint procedure.

However, if instruments of the same type are used, there is also the possibility of confirming sufficient flushability of all the instruments by means of a common, simultaneous check, if the arithmetically determined total throughput volume necessary is obtained on determining the throughput volume on simultaneous throughflow.

The penetrability can be tested by means of fluid from a fluid source being delivered to the or each channel of an instrument, the volume of the fluid which flows through the channel in a unit of time being measured, and the measured fluid volume being compared with preset data specific to the device.

In a preferred embodiment of the method according to the invention, the throughput rate is determined at the outlet side, that is to say after flowing through the channels. In a further variant of the method according to the invention, it is also possible, however, for the fluid quantity flowing through a channel to be determined at the inlet side.

In an alternative embodiment of the invention, the at least one channel of one or more instruments is tested for penetrability by means of this channel being subjected to pressure by delivery of fluid from a pressurized fluid source, the pressure drop over time as a result of a flow of fluid through the channel being measured, and the determined pressure drop being compared with preset data specific to the device. When using fluids with negligible compressibility, the pressure drop per unit of time is directly proportional to the fluid volume emerging from the fluid reservoir and can thus be used for indirect determination of the fluid volume flowing through the channels and capillary tubes in a unit of time.

If the comparison of the test result with preset data specific to the device shows agreement with data known for a specific instrument type or determined in advance, then the instrument subjected to the test is identified as an instrument of this instrument type and is recognized as one that can be flushed. On the basis of this result, the instrument in question is subsequently re-flushed with disinfecting and/or cleaning agents.

In the method according to the invention, a cleaning program, and if appropriate also a disinfection program, provided specifically for this device type is also chosen automatically as a function of the result of the penetrability test, i.e. after identification of the instruments to be cleaned.

If treatment of both non-flexible MIS instruments and endoscopes is required, then the disinfection and cleaning conditions are preferably adapted to the very differing complex inner structure and to the different materials of the instruments which are to be cleaned. This concerns, for example, the concentration of disinfecting and/or cleaning agent in the flushing solution, the duration of flushing or the volume of flushing solution to be used, the temperature during the disinfecting and cleaning method, and also the maximum permissible pressure with which an instrument can be loaded during the method according to the invention.

The method according to the invention in addition provides the possibility of re-flushing the instruments individually or together in groups with disinfecting and/or cleaning agents as a function of the result of the penetrability test. If non-flexible MIS instruments in particular are classified according to the diameter of their inner channel, the instruments can be divided into those with relatively narrow channel diameters, for example 5 mm, and those with relatively large channel diameters, for example 10 mm. On simultaneous re-flushing of instruments having different diameters, there could be, at a given pumping capacity, a risk of individual instruments or individual instrument types being flushed non-uniformly, i.e. not with the previously defined throughflow pressure or throughflow volume.

Instruments with narrow channel diameters are particularly suitable for joint flushing. If a plurality of instruments with relatively large channel diameters are flushed simultaneously, the capacity of the pump which is used may under some circumstances no longer suffice to achieve the previously defined throughflow pressure or the previously set throughflow volume, so that such instruments are preferably re-flushed individually or at most in small groups. By means of these measures it is possible to ensure that all instruments are re-flushed under defined conditions.

The method step of measurement of throughflow also represents a first pre-cleaning. For the disinfecting and cleaning steps which follow this step, there is no need for any particular rearrangements, except for, at most, a change of the fluid source and a metering-in of disinfecting and/or cleaning agent to the fluid present in the reservoir if the fluid used for testing is different than the fluid used for cleaning and disinfection.

In the event of there being no or insufficient throughflow, additional measures can be taken automatically in order to achieve complete flushability. To this end, a pneumatic or hydraulic pressure surge can be used. Alternatively, it is possible, when using a circulating pump for the fluid delivery, to run said pump at increased speed and correspondingly higher pressure; pole-changing centrifugal pumps or positive-displacement pumps can also be used for this purpose. In order to generate high pressures, two pumps can also be connected in series.

If a proper throughput is established, then the test cycle is continued as described. However, if it is still registered that the channel of the instrument in question is obstructed, this device and its position are automatically registered in the microprocessor, and this device can then be removed manually, checked and inserted again.

Following this testing procedure, the instruments which have been accepted are re-flushed from a reservoir charged with cleaning and disinfecting agent(s). The flushing fluid which is used can in this case be collected and returned once more to the reservoir. The fluid from the fluid source is in this case normally delivered by a circulating pump.

Obstinate contamination on surfaces and joints of the instruments can be removed by additional ultrasound treatment.

The testing and cleaning method according to the invention can be followed by sterilization. For example, methods such as ethylene oxide, formaldehyde, $H_2O_2$-plasma and peracetic acid sterilization can be implemented. For this purpose, at least one sterilizing fluid is passed through the channels and over the surfaces of the instruments.

An arrangement for the testing and cleaning of instruments for minimal invasive surgery or minimal invasive examination of body cavities, which can be used in the method according to the invention, comprises:

a testing and cleaning tray for the instruments, which tray has flushing channels, a holder arrangement for the testing and cleaning tray, with attachments for one flushing channel each of the testing and cleaning tray, at least one fluid reservoir which is connected via a distributor to valves and is connected via these to the attachments of the holder arrangement, a pump which is arranged between the fluid reservoir and the distributor, a throughput testing device, and a control arrangement which communicates with the throughput testing device and with the distributor and/or the valves.

In a preferred embodiment of the arrangement, the testing and cleaning tray for the instruments can have end walls with recesses at their upper edges and with bores arranged below the recesses for receiving the instruments, and also connection sleeves. Opening into these connection sleeves are channels which run in the end walls and which emerge from channels running in a base of the testing and cleaning tray with attachment to the attachments of the holder arrangement.

The throughput testing devices used can be, for example, volume-measuring devices or pressure-measuring devices.

The throughput testing device can in this case be arranged on the inlet side in relation to the attachments of the holder arrangement, or on the outlet side in relation to instruments arranged in the holder arrangement.

In the control arrangement, the information transmitted from the throughput testing device is compared with device-specific data preset for standard instruments. If there is agreement between the information transmitted from the testing of an instrument and data stored for an instrument type, the instrument in question is identified as such an instrument and is recognized as being one that can be flushed. Thereupon, the control arrangement transmits the appropriate information to the distributor and the valves in order to effect a cleaning and disinfection of the instrument by targeted admission of cleaning and disinfecting agents.

If the data transmitted from the throughput testing device cannot be assigned to any device-specific standard values in the control arrangement as a result of there being no agreement, the device cannot be identified. The device is consequently recognized as being one that cannot be flushed and is registered for rejection.

In one embodiment of the arrangement, the holder arrangement for the testing and cleaning tray for instruments is provided in a basin by means of which the fluid is collected after it has flowed through the instruments. In this case, the throughput testing device can be arranged behind an outlet of the basin.

In the arrangement, provision is also made to ensure that, after successful testing, not only are the channels and capillary tubes of the instruments cleaned, but also their outer surfaces and joints. Measures suitable for this purpose are known.

In an embodiment in which the holder arrangement is disposed in a basin or a container, ultrasound vibration elements can additionally be provided on the latter in order to remove obstinate contamination from the surfaces and joints of the instruments.

A pressure surge device can additionally be provided in the arrangement, which pressure surge device is in communication with the throughput testing device and is activated in the event of the throughput being insufficient. In the case where the throughput testing device is arranged after the outlet of a basin, a further throughput testing device can additionally be arranged on the inlet side, which additional throughput testing device is arranged between the pressure surge device and the distributor in order to permit, after a pressure surge on account of insufficient throughput, an additional exact registration of the throughput rate.

The fluid reservoir which can be charged with testing, cleaning, disinfecting or sterilizing agent can be provided with a heater for heating the fluids contained therein. By opening a shut-off valve provided on the reservoir and, if so desired, by additionally switching on a tank discharge pump, the reservoir can be emptied; testing, cleaning, disinfecting or sterilizing agents can be metered in via metering pumps which are provided.

In the case where sterilization is additionally intended, the sterilizing fluid is preferably provided in an additional reservoir from which it is delivered to the distributor. In this case too, it is ensured that the sterilizing fluid is also passed over the surfaces of the instruments to be sterilized.

If the holder arrangement with the testing and cleaning tray is arranged in a container, then sterilizing fluid can be additionally introduced into the container, for example via a valve arranged thereon, for the purpose of sterilizing the outer surfaces of the instruments. After sterilization, sterilizing fluid can be withdrawn from the container via this valve, if appropriate using a pump.

A circulating pump can be provided between the fluid reservoir(s) and the distributor. This circulating pump is also necessary, for example when using hydrogen peroxide plasma in the plasma sterilization method, for maintaining the plasma state of the hydrogen peroxide.

A heater can be provided on the fluid reservoir for heating the sterilizing fluid. In order to keep the sterilization temperature constant, an additional heater can furthermore be arranged on a container in which the holder arrangement with the testing and cleaning tray is arranged.

By opening a shut-off valve provided on the fluid reservoir and, if necessary, by additionally switching on a pump, the reservoir can be emptied or filled.

In a particularly preferred embodiment of the arrangement for the testing, cleaning, disinfecting and/or sterilizing of non-flexible MIS instruments, the testing and cleaning tray for MIS instruments, which is shown in FIG. 1 and is described hereinafter, can be used, in which tray the contaminated instruments can undergo all the testing, cleaning and disinfecting steps, described in the methods according to the invention, and also the possible subsequent sterilization by means of a fluid, preferably a plasma, or else in an autoclave, and in which tray they can be stored, so that they are subsequently available for renewed use in operations.

All the testing, cleaning, disinfecting and sterilizing steps according to the invention can moreover be carried out in a common arrangement having the features described for the arrangements which have been described hereinabove, it being possible for the testing and cleaning tray for MIS instruments to be used for treating non-flexible MIS instruments.

Thus, throughout the entire treatment process, the cleaning personnel need come into direct contact with the contaminated instruments only when inserting the contaminated instruments into the testing and cleaning tray. If appropriate, the loaded trays, with the MIS instruments which have been tested for penetrability and have been cleaned and disinfected, may only need to be transferred to sterilization arrangements, so that all the treatment steps require minimal expenditure in terms of work and personnel, which fact brings significant savings in terms of time and costs.

The invention is explained in greater detail hereinbelow with reference to schematic drawings of an exemplary embodiment for non-flexible MIS instruments.

DESCRIPTION OF THE INVENTION

Figure 1:
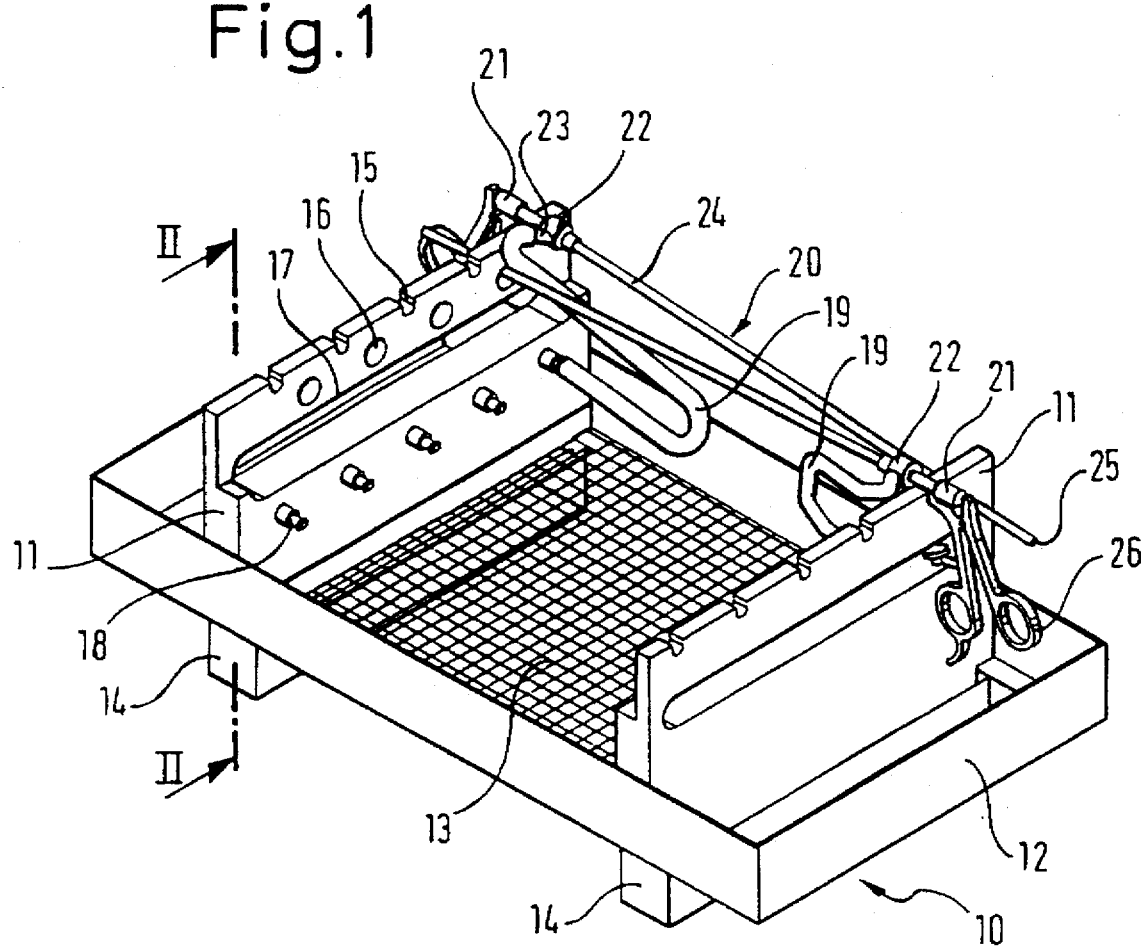
FIG. 1 shows a perspective representation of a testing and cleaning tray for non-flexible MIS instruments.
Figure 2:
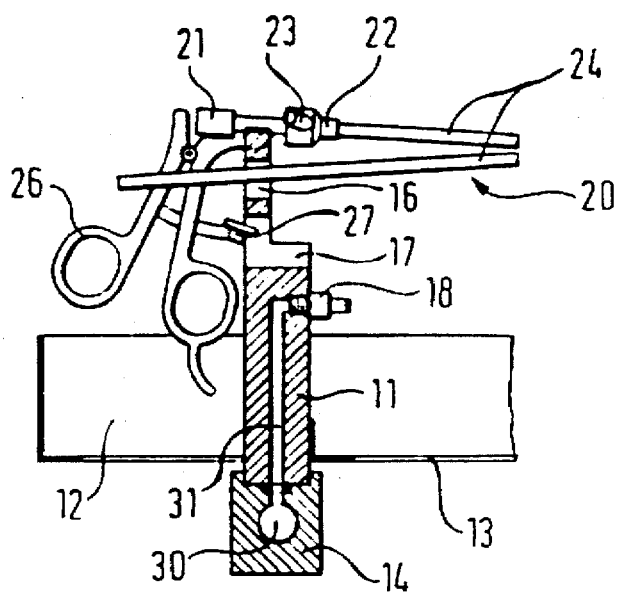
FIG. 2 shows the section II—II in FIG. 1.

The testing and cleaning tray 10 represented in FIGS. 1 and 2 for arrangements for testing and cleaning of non-flexible MIS instruments 20 has rectangular end walls 11 which are connected to each other in axisymmetrical arrangement by means of a horizontal frame 12 bearing on the narrow sides of the end walls 11, and also a grating 13 used as a bottom surface. In the upper third of their vertical extent, the end walls 11 are stepped in such a way that the thickness of the end walls in this area is only a third of the thickness measured in the central area.

The undersides of the end walls 11 are fitted into a recess of a base 14, which recess is provided with a seal. Each of the end walls 11 has, on its top side, semicircular recesses 15 and, further down, an identical number of round bores 16 which are arranged with a gap between them and the recesses 15. Further down still, each of the end walls 11 has a horizontally extending recess 17 which takes up almost the entire width thereof and which half lies in the upper, tapered area of the end wall and half lies in the central area of the end wall.

The end walls 11 are each of identical construction and are arranged in such a way that the semicircular recesses 15 of one end wall 11, if offset downward in parallel, lie exactly opposite the round bores 16 of the other end wall. Situated below the recess 17, in the central area of the end walls 11, there are a number of inwardly directed connection sleeves 18 equal to the number of semicircular recesses 15 and round bores 16. The connection sleeves 18 of one end wall are arranged with a gap between them and the round bores 16 of the same end wall. The connection sleeves 18 are provided for the attachment of pressure hoses 19.

The MIS instruments 20 are received in the testing and cleaning tray 10, between in each case a joint 21 and a connection piece 22 with flushing attachment 23, into the semicircular recesses 15 of the end walls 11 in such a way that a rod-shaped component 24 adjoining the connection piece 22 and with a continuous channel 25 is guided with its open, distal end through the opposite round bore 16 provided on the other side, and in such a way that the MIS instrument 20 is inclined downward in the direction of the open end of its rod-shaped component 24. The open, distal end of the rod-shaped component 24 is situated, in this arrangement, above the interspace between the outwardly facing surface of the end wall 11 and that section of the frame 12 lying opposite it.

A second set of MIS instruments 20 can be arranged in the same way, but starting from the respectively opposite end wall 11, parallel to the first-mentioned MIS instruments, but laterally offset with respect to the latter. A component element 27 arranged on a handle 26 is situated, in this arrangement, with its distal end in the horizontally extending recess 17 of the testing and cleaning tray 10. The flushing attachment 23 provided on the connection piece 22 of the MIS instrument 20 can be connected to the free end of the pressure hose 19 so that the channel 25 leading through the rod-shaped component 24 can be flushed.

FIG. 2 shows the arrangement of the fluid-conveying channels in the testing and cleaning tray 10 which open into the connection sleeves 18. Fluid is guided from a fluid source (not shown) arranged underneath the testing and cleaning tray 10 through horizontal channels 30 in the base 14 of the end walls 1 from which the fluid is conveyed to the connection sleeves 18 via vertically extending channels 31 leading upward in the end walls 11.

Figure 3:
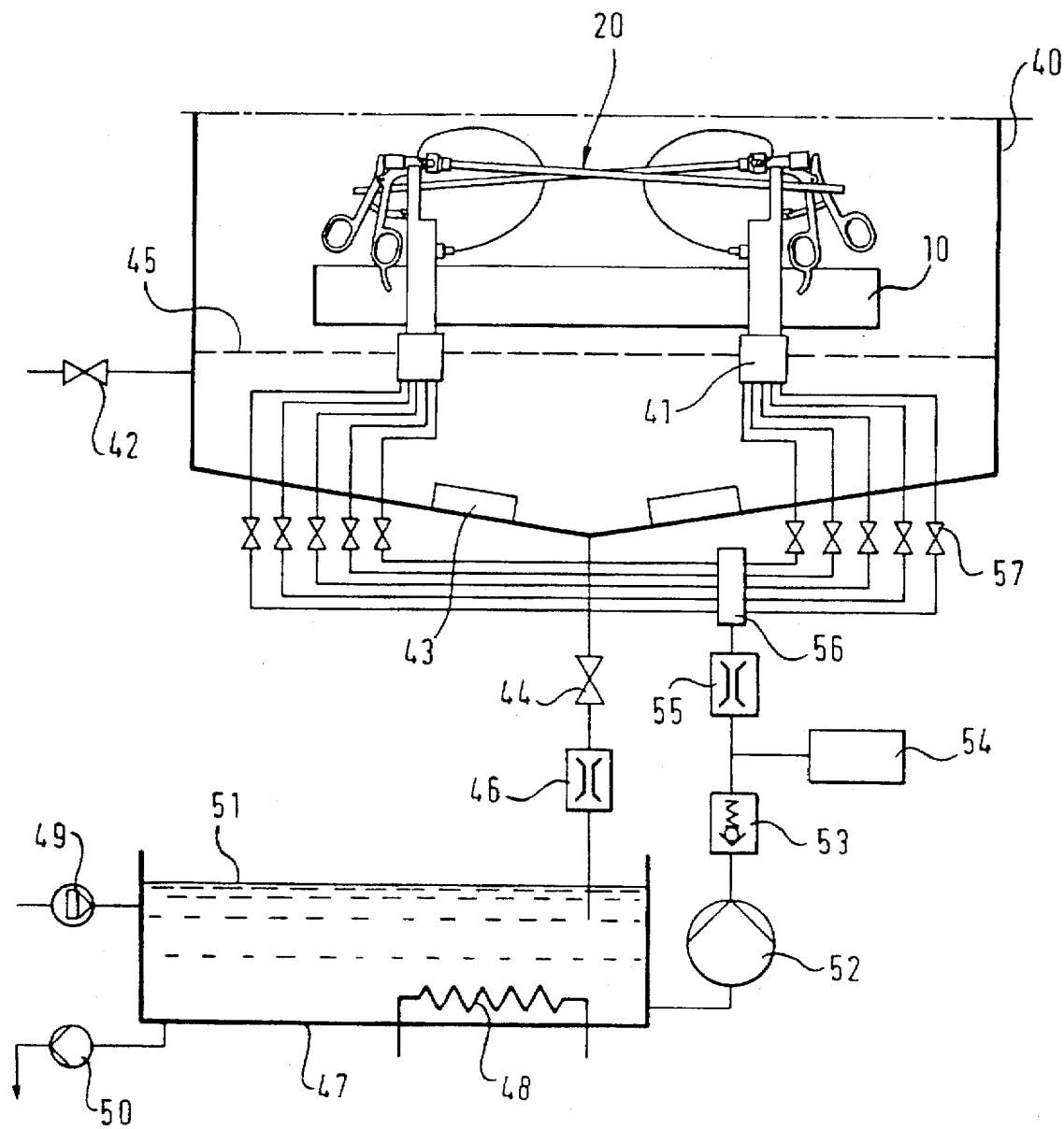
FIG. 3 shows a circuit diagram of an arrangement for the testing and cleaning of MIS instruments with the testing and cleaning tray from FIG. 1.

The arrangement represented in FIG. 3 for the testing and cleaning of MIS instruments has a stainless steel basin 40 which receives a holder arrangement 41. The latter is designed in the form of a connecting block for the testing and cleaning tray 10 loaded with MIS instruments 20 and has attachments for in each case one flushing channel 30. For cleaning the instruments 20, the basin 40 can be filled with fluid via a valve 42, so that the holder arrangement 41 with inserted testing and cleaning tray 10 is covered completely with fluid. The basin 40 is additionally equipped with ultrasound vibration elements 43. By flooding the basin 40 and switching on the ultrasound vibration elements 43, those surface areas of the MIS instruments which are difficult to clean can also be cleaned. The basin 40 has an outlet which can be controlled by a shut-off valve 44, and a level regulator 45 which controls the level of filling of the basin.

Arranged downstream of the shut-off valve 44 of the basin 40 is a throughput testing device 46 which, in the case of a specific embodiment of the testing of the instruments 20, measures the volume of the liquid flowing through after the shut-off valve 44 is opened, which liquid is collected by the basin 40 after defined throughflow of the channels 25 of the MIS instruments 20.

The liquid flowing through the throughput testing device 46 is taken up by a reservoir 47. The reservoir 47 is equipped with a heater 48, and cleaning and disinfecting agent can be metered in via a metering pump 49. An output pump 50 is provided for emptying. The level of filling of the reservoir 47 is controlled by a level regulator 51. Also connected to the reservoir 47 is a circulating pump 52, downstream of which, on the delivery side, a check valve 53 is arranged. Downstream of this check valve are a pressure surge device 54 and a further throughput testing device 55. The cleaning and disinfecting agent is fed, via a distributor 56 provided in connection thereto, to valves 57 which control, via the attachments of the holder arrangement 41, the fluid admission to individual flushing channels 30, 31 in the testing and cleaning tray 10.

In a control arrangement which is not depicted, and which is in contact with one or both throughput testing device(s) 46, 55 and with the distributor 56 and/or the valves 57, the information transmitted from the throughput testing device (s) 46, 55 is compared with device-specific data preset for standard MIS instruments 20. If there is agreement between the information transmitted from the testing of an MIS instrument 20 and the data stored for an MIS instrument type, the instrument 20 in question is identified as such an instrument and is recognized as being one that can be flushed through. The control arrangement thereupon transmits the appropriate information to the distributor 56 and the valves 57 in order to effect a cleaning and disinfection of the MIS instrument 20 by admission of cleaning and disinfecting agents.

If the data transmitted from the throughput testing device (s) 46, 55 cannot be assigned in the control arrangement to any device-specific standard values on account of there being no agreement, the instrument 20 cannot be identified. The instrument 20 is consequently recognized as being one that cannot be flushed through and is registered for rejection.

An arrangement for sterilizing MIS instruments 20 can be deduced from FIG. 3. The arrangement includes a container 40 which, as is indicated by a dot-and-dash line, replaces the component 40, and a holder arrangement 41 which is arranged in the interior of the container 40. The holder arrangement 41 is designed in the form of a connecting block for the testing and cleaning tray (FIG. 1) loaded with MIS instruments 20 and has attachments for in each case one flushing channel 30. The container 40 can be filled with sterilizing fluid, which may be pressurized, via a valve 42, so that sterilizing fluid flows all through the holder arrangement 41 with inserted testing and cleaning tray 10. The container 40 has an outlet which can be controlled via a shut-off valve 44 and which is connected to a reservoir 47 for sterilizing fluid. The fluid reservoir 47 is equipped with a heater 48 and can be filled or emptied by means of a pump 50. Also connected to the fluid reservoir 47 is a circulating pump 52, downstream of which, on the delivery side, a check valve 53 is arranged. Sterilizing fluid is fed, via a distributor 56 provided in connection thereto, to valves 57 which control, via the attachments of the holder arrangement 41, the fluid admission to individual flushing channels 30, 31 in the testing and cleaning tray 10.

The components bearing the references 43, 45, 46, 49, 51, 54, 55 are not necessary for the sterilizing of MIS instruments 20 in the arrangement according to the invention.

Figure 4:
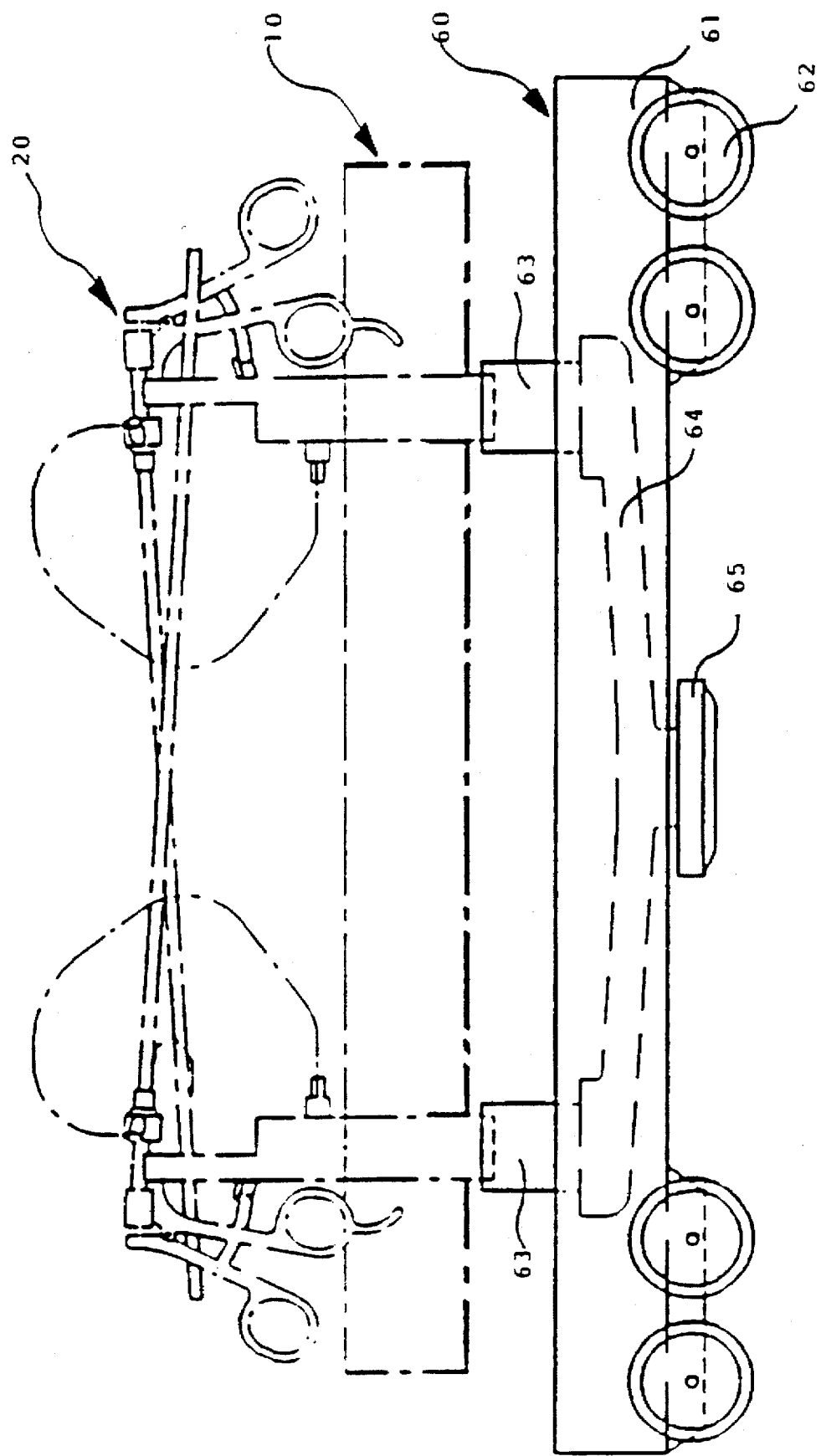
FIG. 4 shows the testing and cleaning tray according to FIG. 1 placed in a washing basket of a washing and disinfecting machine.

FIG. 4 is a schematic representation of the testing and cleaning tray 10 from FIG. 1 placed in a washing basket 60 of a washing and disinfecting machine (not shown). The washing basket 60 comprises a flat basin 61 which is guided on rollers 62, which makes it easier to push into washing and disinfecting machines. The testing and cleaning tray 10 is received by inserts 63 in the basin 61 of the washing basket 60, via the bottom surfaces of the bases 14 of the end walls 11, both inserts 63 being received in turn by a connection element 64 which extends on the underside of the basin 61 and is provided centrally with an attachment 65.

Fluid can be conveyed from a fluid source (not shown), if appropriate via a distributor and downstream valves, to the attachment 65 of the connection element 64. Starting from the attachment 65, the fluid then flows through one or more opened channels provided in the connection element 64 to the inserts 63 and from there to channels 30 extending in each case in the bases 14 of the testing and cleaning tray 10. The fluid can thereafter flush through the adjoining channels 31 and then the channels 25 of the MIS instruments 20 passing through the rod-shaped components By adapting the testing and cleaning tray for use for endoscopes, by means of providing connection sleeves for complete throughflow of all channels and capillary tubes, the arrangements can be used without further modifications for the testing, cleaning, disinfecting and/or sterilizing of endoscopes.

I claim:

1. A method for the testing and cleaning of one or more instruments for minimal invasive surgery or minimal invasive examination of body cavities, each instrument including at least one continuous channel connected to a fluid source, said method comprising the steps of:

conveying fluid to said at least one channel from said fluid source and measuring the throughput of fluid through said at least one channel;

comparing said measured throughput with preset throughput data specific to the types of instruments being tested;

identifying an instrument to set aside as unflushable where its measured throughput does not match any of the preset throughput data;

identifying an instrument as flushable where said measured throughput matches one of said preset throughput data;

identifying by type each flushable instrument by means of the preset throughput data to which it corresponds;

establishing conditions for flushing each flushable instrument channel with disinfecting and/or cleaning agents based on the identified instrument type; and flushing each flushable instrument channel with disinfecting and/or cleaning agents according to the conditions established for flushing each flushable instrument channel.

2. The method of claim 1 wherein said measuring step comprises measuring each instrument individually with said fluid being conveyed only to said at least one channels of said individual instrument being measured.

3. The method of claim 1 wherein said measuring step comprises measuring a plurality of said instruments jointly with said fluid being conveyed to all of said at least one channels in parallel.

4. The method of claim 1 wherein said measuring step comprises measuring a volume of said fluid flowing through said at least one channel in a unit of time.

5. The method of claim 1 wherein said measuring step comprises:

pressurizing said at least one channel by conveying fluid from said fluid source; and measuring a pressure drop over time as a result of a flow of said fluid through said at least one channel.

6. The method of claim 1 further comprising the step of automatically implementing an increase in pressure of the fluid applied to said at least one channel to achieve complete throughput of said instruments identified to be set aside.

7. The method of claim 1 further comprising step of automatically implementing by compressed air a pressure surge in the fluid supplied to said at least one channel to achieve complete throughput of said instrument identified to be set aside.

8. The method of claim 1 wherein said flushing step is performed on a plurality of said flushable instruments either individually or in groups.

9. The method of claim 1 further comprising the step of detaching obstinate contamination of said instruments using ultrasound.

10. The method of claim 1 further comprising the step of sterilizing said instruments, after testing and cleaning, by means of a least one sterilizing fluid being conveyed through said at least one channel of said instruments and over surfaces thereof.

11. The method of claim 10 wherein said sterilizing fluid is ethylene oxide, formaldehyde, $H_2O_2$ plasma or peracetic acid.

* * * * *